United States Patent [19]
Crosby et al.

[11] Patent Number: 5,820,552
[45] Date of Patent: *Oct. 13, 1998

[54] SONOGRAPHY AND BIOPSY APPARATUS

[75] Inventors: Peter Andrew Crosby, Greenwood Village, Colo.; Ascher Shmulewitz, Mercer Island, Wash.

[73] Assignee: United States Surgical Corporation, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 680,559

[22] Filed: Jul. 12, 1996

[51] Int. Cl.$^6$ ........................................ A61B 6/04
[52] U.S. Cl. .......................... 600/407; 600/439; 128/915; 128/660.03; 378/37
[58] Field of Search ............................ 128/660.03, 653.1, 128/915; 378/37; 606/130; 600/407, 439

[56] References Cited

U.S. PATENT DOCUMENTS

| | | |
|---|---|---|
| Re. 30,397 | 9/1980 | King . |
| 2,707,662 | 5/1955 | Goldfield et al. . |

(List continued on next page.)

FOREIGN PATENT DOCUMENTS

| | | |
|---|---|---|
| 105 812 | 4/1984 | European Pat. Off. . |
| 483 005 | 4/1992 | European Pat. Off. . |
| 581 704 | 2/1994 | European Pat. Off. . |
| 23 35 576 | 1/1975 | Germany . |
| 3226976 | 2/1983 | Germany . |
| 33 22 053 | 12/1983 | Germany . |
| 32 27 624 | 1/1984 | Germany . |
| 34 05 537 | 8/1985 | Germany . |
| 34 47 444 | 7/1986 | Germany . |
| 40 37 387 | 5/1992 | Germany . |
| 896 539 | 4/1980 | U.S.S.R. . |
| 2 094 590 | 9/1982 | United Kingdom . |
| 83/02053 | 6/1983 | WIPO . |
| 88/08272 | 11/1988 | WIPO . |
| 94/21189 | 9/1994 | WIPO . |
| 95/11627 | 5/1995 | WIPO . |

OTHER PUBLICATIONS

Magnusson, A., "New Stereotactic Instrument Facilitates Computer Tomographically Guided Punctio", Läkartidningen, vol. 86, No. 21, pp. 1885–1886, (1988).

Gardineer et al., "Video–photographic System for Rapid Inexpensive Unit Recording and Flexible Replay of Real–time Ultrasonic Imaging of the Breast", SPIE vol. 273, Appln. of Optical Instrumentation in Medicine IX, pp. 343–347 (1981).

Bruno D. Fornage, MD et al., Breast Masses: US–Guided Fine–Needle Aspiration Biopsy[1], Radiology, 162:409–414 (1987).

B.D. Fornage, MD et al., "Ultrasound–Guided Needle Biopsy of the Breast and Other Interventional Procedures", vol. 30, No. 1, pp. 167–185 (Jan. 1992).

Darla Haight et al., "Radiologists Spread Their Wings: A Look at the Possibilities in STereotactic Breast Biopsy", Admin. Rad. J., pp. 87–89 (Nov. 1987).

E. Azavedo et al., "Stereotactic Fine–Needle Biopsy in 2594 Mammographically Detected Non–Palable Lesions", The Lancet, pp. 1033–1036 (May 1989).

Eva Rubin, MD, "Breast Cancer in the 90's", Applied Radiology, pp. 23–26 (Mar. 1993).

(List continued on next page.)

Primary Examiner—Marvin M. Lateef
Assistant Examiner—Shawna J. Shaw

[57] ABSTRACT

Apparatus for conducting an imaging examination and/or biopsy of biological tissue that enable a patient to remain in an inclined, seated orientation, so that the tissue is readily presented for examination and biopsy, while the examination and biopsy site is screened from the patient's view. Apparatus also provided for enhancing imaging of the patient's tissue near the chest wall, and for conducting image-guided biopsy.

14 Claims, 7 Drawing Sheets

U.S. PATENT DOCUMENTS

| | | |
|---|---|---|
| 3,165,630 | 1/1965 | Bielat et al. . |
| 3,420,097 | 1/1969 | Battermann et al. . |
| 3,480,002 | 11/1969 | Flaherty et al. . |
| 3,556,081 | 1/1971 | Jones . |
| 3,589,361 | 6/1971 | Loper . |
| 3,609,355 | 9/1971 | Kwarzen . |
| 3,765,403 | 10/1973 | Brenden . |
| 3,921,442 | 11/1975 | Soloway . |
| 3,939,696 | 2/1976 | Kossoff . |
| 3,963,933 | 6/1976 | Henkes, Jr. . |
| 3,971,950 | 7/1976 | Evans et al. . |
| 3,973,126 | 8/1976 | Redington et al. . |
| 3,990,300 | 11/1976 | Kossoff . |
| 3,991,316 | 11/1976 | Schmidt et al. . |
| 4,021,771 | 5/1977 | Collins et al. . |
| 4,051,380 | 9/1977 | Lasky . |
| 4,058,114 | 11/1977 | Soldner . |
| 4,094,306 | 6/1978 | Kossoff . |
| 4,099,880 | 7/1978 | Kano . |
| 4,167,180 | 9/1979 | Kossoff . |
| 4,206,763 | 6/1980 | Pedersen . |
| 4,249,541 | 2/1981 | Pratt . |
| 4,285,010 | 8/1981 | Wilcox . |
| 4,343,799 | 8/1982 | Heckler . |
| 4,347,850 | 9/1982 | Kelly-Fry et al. . |
| 4,363,326 | 12/1982 | Kopel . |
| 4,369,284 | 1/1983 | Chen . |
| 4,402,324 | 9/1983 | Lindgren et al. . |
| 4,433,690 | 2/1984 | Green et al. . |
| 4,434,799 | 3/1984 | Taenzer . |
| 4,455,872 | 6/1984 | Kossoff et al. . |
| 4,465,069 | 8/1984 | Barbier et al. . |
| 4,469,106 | 9/1984 | Harui . |
| 4,485,819 | 12/1984 | Igl . |
| 4,497,325 | 2/1985 | Wedel . |
| 4,501,278 | 2/1985 | Yamaguchi et al. . |
| 4,527,569 | 7/1985 | Kolb . |
| 4,541,436 | 9/1985 | Hassler et al. . |
| 4,545,385 | 10/1985 | Pirschel . |
| 4,573,180 | 2/1986 | Summ . |
| 4,579,123 | 4/1986 | Chen et al. . |
| 4,583,538 | 4/1986 | Onik et al. . |
| 4,592,352 | 6/1986 | Patil . |
| 4,599,738 | 7/1986 | Panetta et al. . |
| 4,608,989 | 9/1986 | Drue . |
| 4,613,122 | 9/1986 | Manabe . |
| 4,613,982 | 9/1986 | Dornheim et al. . |
| 4,618,213 | 10/1986 | Chen . |
| 4,618,973 | 10/1986 | Lasky . |
| 4,625,555 | 12/1986 | Fujii . |
| 4,671,292 | 6/1987 | Matzuk . |
| 4,681,103 | 7/1987 | Boner et al. . |
| 4,686,997 | 8/1987 | Oloff et al. . |
| 4,722,346 | 2/1988 | Chen . |
| 4,727,565 | 2/1988 | Ericson . |
| 4,733,661 | 3/1988 | Palestrant . |
| 4,735,215 | 4/1988 | Goto et al. . |
| 4,750,487 | 6/1988 | Zanetti . |
| 4,774,961 | 10/1988 | Carr . |
| 4,784,134 | 11/1988 | Arana . |
| 4,791,934 | 12/1988 | Brunnett . |
| 4,821,727 | 4/1989 | Levene et al. . |
| 4,844,080 | 7/1989 | Frass et al. . |
| 4,862,893 | 9/1989 | Martinelli . |
| 4,869,247 | 9/1989 | Howard, III et al. . |
| 4,875,478 | 10/1989 | Chen . |
| 4,890,311 | 12/1989 | Saffer . |
| 4,898,178 | 2/1990 | Wedel . |
| 4,899,756 | 2/1990 | Sonek . |
| 4,911,173 | 3/1990 | Terwilliger . |
| 4,930,143 | 5/1990 | Lundgren et al. . |
| 4,940,061 | 7/1990 | Terwilliger et al. . |
| 4,944,308 | 7/1990 | Akerfeldt . |
| 4,953,558 | 9/1990 | Akerfeldt . |
| 4,962,515 | 10/1990 | Kopans . |
| 4,962,752 | 10/1990 | Reichenberger et al. . |
| 4,966,152 | 10/1990 | Gäng et al. . |
| 4,981,142 | 1/1991 | Dachman . |
| 5,003,979 | 4/1991 | Merickel et al. . |
| 5,007,428 | 4/1991 | Watmough . |
| 5,029,193 | 7/1991 | Saffer . |
| 5,056,523 | 10/1991 | Hotchkiss, Jr. et al. . |
| 5,078,142 | 1/1992 | Siczek et al. . |
| 5,078,149 | 1/1992 | Katsumata et al. . |
| 5,083,305 | 1/1992 | Tirelli et al. . |
| 5,095,910 | 3/1992 | Powers . |
| 5,099,503 | 3/1992 | Strömmer . |
| 5,107,843 | 4/1992 | Aarnio et al. . |
| 5,113,420 | 5/1992 | Davis, Jr. et al. . |
| 5,158,088 | 10/1992 | Nelson et al. . |
| 5,199,056 | 3/1993 | Darrah . |
| 5,205,297 | 4/1993 | Montecalvo et al. . |
| 5,219,351 | 6/1993 | Teubner et al. . |
| 5,260,871 | 11/1993 | Goldberg . |
| 5,262,468 | 11/1993 | Chen . |
| 5,273,435 | 12/1993 | Jacobson . |
| 5,280,427 | 1/1994 | Magnusson et al. . |
| 5,305,365 | 4/1994 | Coe . |
| 5,318,028 | 6/1994 | Mitchell et al. . |
| 5,361,768 | 11/1994 | Webler et al. . |
| 5,379,769 | 1/1995 | Ito et al. . |
| 5,386,447 | 1/1995 | Siczek . |
| 5,396,897 | 3/1995 | Jain et al. . |
| 5,411,026 | 5/1995 | Carol . |
| 5,415,169 | 5/1995 | Siczek et al. . |
| 5,426,685 | 6/1995 | Pellegrino et al. . |
| 5,433,202 | 7/1995 | Mitchell et al. . |
| 5,447,154 | 9/1995 | Cinquin et al. . |
| 5,450,851 | 9/1995 | Hancock . |
| 5,474,072 | 12/1995 | Shmulewitz . |
| 5,479,927 | 1/1996 | Shmulewitz . |
| 5,487,387 | 1/1996 | Trahey et al. . |
| 5,488,952 | 2/1996 | Schoolman . |
| 5,499,989 | 3/1996 | LaBash . |
| 5,506,877 | 4/1996 | Niklason et al. . |
| 5,522,787 | 6/1996 | Evans . |
| 5,524,636 | 6/1996 | Sarvazyan et al. . |
| 5,594,769 | 1/1997 | Pellegrino et al. . |
| 5,595,177 | 1/1997 | Mena et al. . |
| 5,603,326 | 2/1997 | Richter . |
| 5,609,152 | 3/1997 | Pellegrino et al. . |
| 5,640,956 | 6/1997 | Getzinger et al. . |
| 5,660,185 | 8/1997 | Shmulewitz et al. . |
| 5,664,573 | 9/1997 | Shmulewitz et al. . |

OTHER PUBLICATIONS

Ellen B. Mendelson, MD, "Ultrasound Secures Place in Breast Ca Management", Diagnostic Imaging, pp. 120–129 (Apr. 1991).

Ferris H. Hall, MD, "Mammographic Second Opinions Prior to Biopsy of Nonpalpable Beast Lesions", Arch Surg, vol. 125, pp. 298–299 (Mar. 1990).

Gunilla Svane, MD., "Stereotactic Needle Biopsy", Dept. of Dianostic Radioloyg at the Karolinska Hospital, Stockholm, Sweden (1987).

Gillian Newstead, MD., "When and When Not to Biopsy the Breast", Diagnostic Imaging, pp. 111–116, (Mar. 1993).

Ingvar Andersson, MD, "Medical Radiography and Photography", vol. 62, No. 2, pp. 2–41 (1986).

Jan Bolmgren, et al., "Stereotaxic Instrument for Needle Biopsy of the Mamma", (Sweden) J. Radiology, 129:121–125 (Jul. 1977).

Kambiz Dowlatshahi, MD, Breast Care: "The Needle Replaces The Knife" (Exploring Sterotactic Guided Needle Biopsy), Admin. Radiology, pp. 28–31 (Jun. 1989).

K. Dowlatshahi, MD, "Palpable Breast Tumors: Dianosis with Stereotaxic Localization and Fine–Needle Aspiration[1]", Radiology 170, No. 2, pp. 427–433 (Feb. 1989).

Ralph Mösges et al., "Multimodal Information for Computer–Integrated Surgery", Mösges & Lavallée: Multimodal Information for CIS/Data Acquisition & Segmentation, pp. 5–19.

Rachel F. Brem, MD et al., "Template–guided Breast US[1]", Radiology 184:872–874 (Sep. 1992).

Steve H. Parker, MD et al., "Percutaneous Large–Core Breast Biopsy: A Multi–institutional Study[1]", Radiology vol. 193, No. 2, pp. 359–364 (Nov. 1994).

S.H. Parker, MD et al., "Large–Core Breast Biopsy Offers Reliable Diagnosis", Diagnostic Imaging, 8 pages (Oct. 1990).

S.H. Parker, MD et al. "US–guided Automated Large–Core Breast Biopsy[1]", Radiology, 187:507–511 (May 1993).

P.N.T. Wells et al., "Tumor detection by ultrasonic Doppler blood–flow signals", Ultrasonics, pp. 231–232 (Sep. 1977).

Valerie P. Jackson, MD, "The Role of US in Breast Imaging[1]", Radiology 177:305–311 RSNA (Nov. 1990).

W. Phil Evans, MD et al., "Needle Localization and Fine–Needle Aspiration Biopsy of Nonpalpable Breast Lesions with use of Standard and Stereotactic Equipment", Radiology, 173:53–56 (1989).

William F. Conway, MD et al., "Occult Breast Masses: Use of a Mammographic Localizing Grid for US Evaluation[1]", Radiology, 181:143–146 (1991).

SONOGRAPHY AND BIOPSY APPARATUS

BACKGROUND OF THE INVENTION

This invention relates to methods and apparatus for conducting an examination of breast tissue and for performing biopsy of that tissue. In particular, the present invention provides methods and apparatus for supporting a patient in an orientation that enhances imaging capability, while enabling the patient to be comfortably positioned during the biopsy procedure.

Previously known biopsy methods range from minimally invasive techniques, such as fine needle aspiration (using, for example, a 21 gauge hypodermic needle) and large core biopsy (using, for example, a 14 gauge needle mounted in an automated biopsy gun), to open-procedures in which the lesion is surgically excised. Minimally invasive techniques are faster, less expensive, safer and less traumatic for the patient than surgical excision, and have begun developing widespread acceptance.

Free-hand ultrasound techniques, in which insertion of a biopsy needle into a suspected lesion is performed by holding a linear array ultrasound transducer in one hand and inserting the needle into the tissue with the other hand, are described, for example, in Fornage et al., "Ultrasound-Guided Needle Biopsy Of The Breast And Other Interventional Procedures," Radiologic Clinics Of North America, Vol. 30, No. 1 (January 1992), Fornage et al. "Breast Masses: US-Guided Fine Needle Aspiration Biopsy," Radiology, 162:409–414 (February 1987), Parker et al., "US-guided Automated Large-Core Breast Biopsy," Radiology, 187:507–511 (May 1993), and Parker and Jobe, "Large-Core Breast Biopsy Offers Reliable Diagnosis," Diagnostic Imaging (October 1990).

In the techniques described in the foregoing articles, an ultrasound transducer is held above the midline of the suspicious mass and the needle (or cannula of the automated biopsy gun) is then inserted in the tissue near the base of the transducer, so that the tip of the needle appears in the ultrasound scan. In addition, when a biopsy gun is employed, additional personnel may be required to steady the biopsy gun during use or to hold the ultrasound transducer.

As described in the Fornage et al. articles and Parker et al. article, difficulties arise using the freehand technique where the suspected lesion is located near the patient's chest wall, or in proximity to a prothesis. These articles also emphasize that the practitioner's level of skill in using the free-hand technique can dramatically influence the results obtained. All of the foregoing articles reject the use of biopsy needle guides that can be attached to the ultrasound transducer, because the guides are said to interfere with the flexibility and maneuverability required to obtain satisfactory results.

The Parker and Jobe article also describes stereotactic mammographic biopsy systems. In such systems, two X-ray images of the breast tissue are made at different angles, thereby permitting the coordinates of a lesion to be calculated. The biopsy device, typically an automated biopsy gun (e.g., Biopty from C. R. Bard, Inc., Bard Urological Division, Covington, Ga.) mounted in a rigid housing attached to the biopsy table, is moved to the calculated coordinates and actuated. Two additional X-ray views of the breast tissue are then taken to confirm that the needle has actually sampled the region of the suspected lesion. The article further describes that in stereotactic systems breast movement may render earlier stereo calculations of little use.

A general disadvantage of these previously known methods and apparatus is level of anxiety and discomfort generally experienced by the patient during the scanning and biopsy procedures. In the case of the free-hand ultrasound examination and biopsy procedure, the patient generally can observe the clinician's activities, including the insertion and withdrawal of the aspiration (or large core biopsy needle).

Since multiple samples are typically required, the patient experiences not only immediate pain and discomfort during needle insertion, but may also experience heightened anxiety due to the anticipated pain of further insertions and the presence of bleeding from the wounds. Such emotional distress may create additional hazards for both the patient and clinician should the patient faint during the procedure.

In the case of stereotactic biopsy systems, the patient's anxiety may tend to be further heightened due to unfamiliarity with the technology employed. Previously known stereotactic biopsy systems generally require the patient to lay prone on an elevated table, and to insert a breast through an opening in the table. Patient's undergoing biopsy using such equipment must not only endure the discomfort of the biopsy procedure itself, but are also expected to experience feelings of anxiety, discomfort, and vulnerability arising from the strangeness of the technology and the unfamiliar prone position required by such systems.

Similarly, Brenden U.S. Pat. No. 3,765,403 describes ultrasound apparatus wherein the patient lies prone on a patient supporting surface while her breast is immersed in a water-filled tank. Taenzer U.S. Pat. No. 4,434,799 also describes an immersion bath system wherein the patient's breast is immobilized between an ultrasonic transducer and ultrasonic receiving transducer. Neither system described in these patents addresses important issues of patient comfort, nor do these devices provide any capability for performing tissue biopsies.

Another drawback of previously-known imaging and biopsy systems, including the stereotactic systems, is the considerable cost and size of such systems. In particular, because previously known imaging and biopsy systems are both costly and require dedicated space, they typically are not affordable, either in cost or in terms of office space available, to the average clinic or group of health practitioners. Accordingly, stereotactic systems and other dedicated biopsy systems are generally found only in larger clinics and hospitals, and the benefits afforded by such technology are not conveniently available to many patients.

Moreover, the size of previously known imaging and biopsy systems is typically too large to allow such systems to be conveniently transported to a patient community for volume screening of patients. For example, because the typical subject for breast screening involves an older portion of the population, the size of previously known imaging and biopsy systems has prevented such systems from being readily transported, for example, to elderly community centers for large scale screening.

In view of the foregoing, it would be desirable to provide apparatus and methods for performing tissue imaging and biopsy that enable a patient to be comfortably oriented during the procedure, and which apparatus and methods lessen both the patient's physical pain and discomfort as well as the patient's emotional stress and anxiety during the procedure.

It also would be desirable to provide apparatus and methods for performing tissue imaging and biopsy that not only provide the patient with a psychological sense of well-being during a procedure, but which facilitate removing the patient quickly and safely in the event the patient experiences dizziness or fainting during the procedure.

It further would be desirable to provide apparatus and methods for performing tissue imaging and biopsy that enable the clinician to have access to the patient's tissue, including near the chest wall, but in a manner so that the patient maintains a comfortable orientation and the site of the biopsy is screened from the patient's view.

It would further be desirable to satisfy the unmet need for imaging and biopsy systems that are both economical and require less space than previously known systems, thus enabling a larger segment of the health community to offer patients the benefits of breast screening at affordable pricing.

It would further be desirable to provide imaging and biopsy systems that can be readily transported to concentrations of potential patients, thus making the benefits of breast screening technology readily available to a larger segment of the target population.

SUMMARY OF THE INVENTION

In view of the foregoing, it is an object of this invention to provide apparatus and methods for performing imaging and biopsy of tissue that enable a patient to be comfortably oriented during the procedure, and which apparatus and methods lessen both the patient's physical pain and discomfort as well as the patient's emotional stress and anxiety during the procedure.

It is another object of the present invention to provide apparatus and methods for performing tissue imaging and biopsy that not only provide the patient with a psychological sense of well-being during a procedure, but which also facilitate removing the patient quickly and safely in the event that the patient experiences dizziness or fainting during the procedure.

It is another object of this invention to provide apparatus and methods for performing tissue imaging and biopsy that enables the clinician to have access to the patient's tissue, including near the chest wall, but in a manner so that the patient maintains a comfortable orientation and the site of the biopsy is screened from the patient's view.

It is a further object of this invention to provide methods and apparatus for imaging and biopsy tissue that are both economical and require less space than previously known systems, thus enabling a larger segment of the health community to offer patients the benefits of breast screening at affordable pricing.

It is yet another object of this invention to provide apparatus for imaging and biopsy of tissue, and methods for using such apparatus, that can be readily transported to concentrations of potential patients, thus making the benefits of breast screening technology readily available to a larger segment of the target population.

These and other objects of the invention are accomplished in accordance with the principles of the invention by providing a stand for use in imaging and biopsy of a patient's tissue that both supports the patient and permits the patient to a assume a relaxed orientation. In particular, the apparatus of the present invention permits the patient to assume a seated, slightly inclined position so that the patient's legs, torso, arms and head are supported, but in an orientation that does create a psychological sense of vulnerability in the patient.

In a preferred embodiment, the apparatus of the present invention provides a slightly inclined stand at which a patient may be seated. One of the patient's breasts is inserted through an opening in the stand and the patient inclines forward so that her torso and head is supported by a bearing surface of the stand. Hand grips are provided at the circumference of the stand to assist the patient in orienting herself with respect to the stand, as well as providing surfaces that the patient may grasp during the biopsy procedure to alleviate anxiety and emotional distress. Adjustable foot supports are likewise provided to support the patient's legs.

In accordance with the preferred embodiment, the breast inserted through the opening in the bearing surface of the stand is compressed between opposing compression surfaces for imaging, which may be either radiographic or preferably by using an ultrasound transducer. An optional biopsy system is also provided for obtaining tissue samples where indicated, and positioning of the biopsy system may be guided using the ultrasound transducer.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
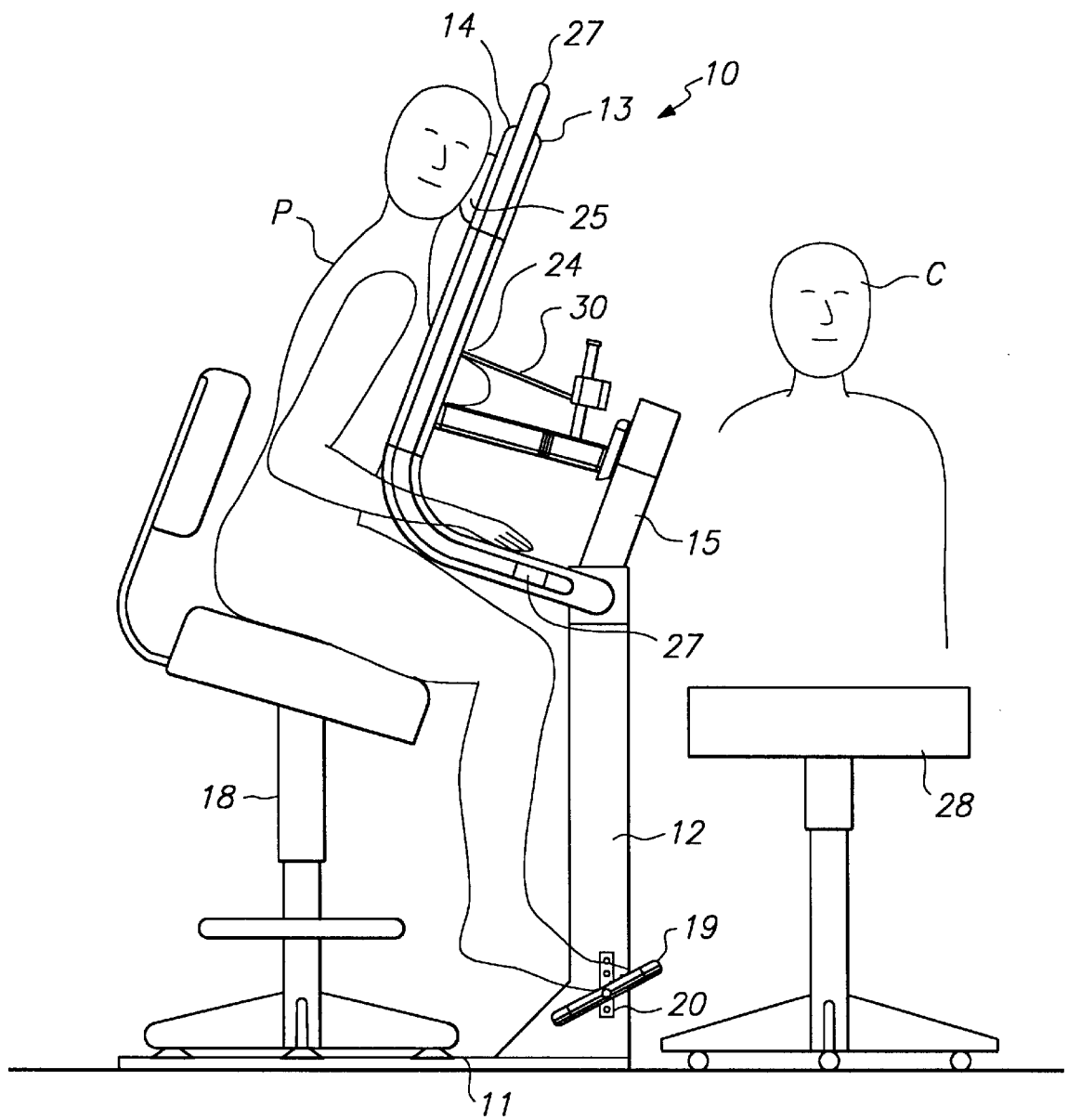
FIG. 1 is an elevation view of an illustrative embodiment of the patient support apparatus or stand of the present invention.
Figures 2, 3:
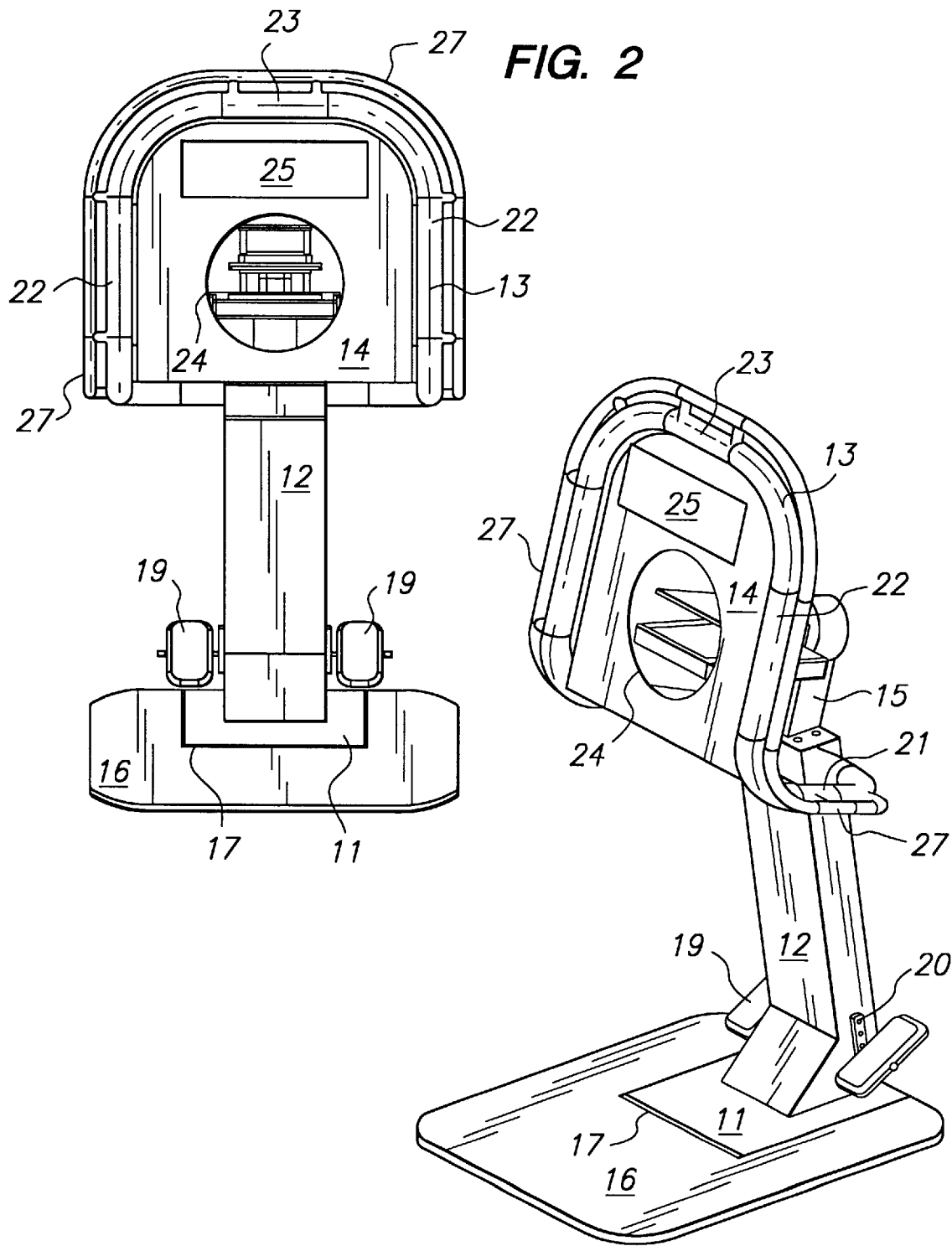
FIG. 2 is a frontal view of the stand of FIG. 1 at an angle orthogonal to the patient bearing surface.
FIGS. 3 and 4 are, respectively, perspective views from the front and rear of the stand of FIG. 1.
Figure 4:
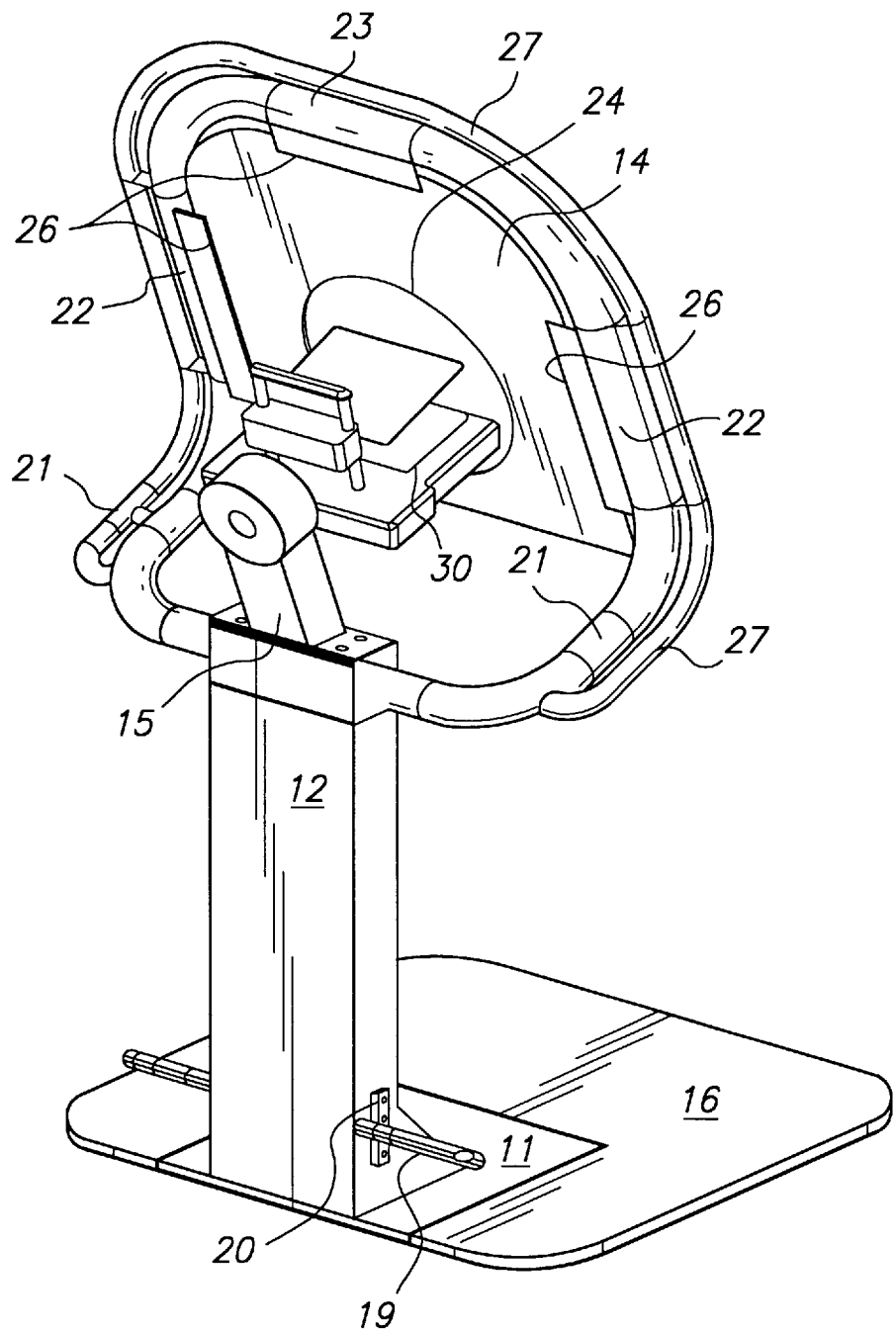

The present invention is described with respect to an illustrative system for performing imaging of biological tissue, and for conducting biopsy of such tissue, which at both the system level and component level represent significant advances over previously known technology for imaging and biopsy of tissue. In particular, the present invention includes novel features directed to (1) a patient support stand for use in imaging and/or biopsy of tissue, (2) apparatus and method for inducing traction in biological tissue to be imaged and/or biopsied, and (3) apparatus and methods for image-guided biopsy of tissue.

While the features of the present invention are described in the context of a stand useful for ultrasound imaging and image-guided biopsy of biological tissue, it will be readily appreciated by those of skill in the art, that the various novel features of the present invention may be advantageously employed in a variety of contexts, including with standard radiographic imaging techniques. The following descriptions of the components and methods of the present invention should therefore be understood as illustrative only.

Patient Support Apparatus

Referring to FIGS. 1 to 4, an illustrative embodiment of a patient support apparatus or stand 10 constructed in accordance with the present invention is described. Stand 10 comprises base 11, vertical pillar 12, frame 13 supporting patient bearing surface 14 and imaging system support column 15.

Vertical pillar 12 is fastened to base 11 using conventional fastening means, e.g., bolts, or may be welded. Nonslip mat 16 may comprise a rubber sheet overlying a plywood, plastic or metal plate, and includes cutout 17 to fit snugly around base 11. Nonslip mat 16 ensures that chair 18, upon which patient P is seated, does not slide away from stand 10 when the patient inclines onto patient bearing surface 14 as shown in FIG. 1.

Vertical pillar 12 carries foot supports 19 which may be vertically adjustably positioned in holes 20 on vertical pillar 12 to accommodate the patient's height. Vertical pillar 12 is preferably constructed of metal plate, e.g., steel, welded along the edges to form a hollow box-like configuration, so that electrical cable associated with the imaging system may pass through the interior of vertical pillar 12.

Frame 13 is preferably formed of thin-walled metal or metal alloy tubing and is connected to the upper lateral surfaces of vertical pillar 12 by suitable means, e.g., by bolts or welds. Frame 13 includes substantially horizontal arms 21, vertical frame elements 22 and top connecting member 23 joining the upper ends of vertical frame elements 22. Horizontal arms 21, vertical frame elements 22 and top connecting member 23 may be permanently fastened together by welding, or other suitable means. Alternatively, the tubing used to manufacture the components of frame 13 may have stepped outer diameters so that the frame elements may be removably interlocked with one another, thereby permitting disassembly of the frame to enhance portability.

Patient bearing surface 14 is carried within frame 13 along its periphery to support the weight of the patient's torso when the patient is inclined against bearing surface 14, and includes opening 24 through which the patient extends a breast for imaging or biopsy, as described hereinbelow. Patient bearing surface 14 may comprise a thin, rigid, plastic or metal alloy backing covered by a thin layer of medium density closed cell foam padding. The foam padding of patient bearing surface 14 may in addition be covered with a cleanable, breathable fabric, that will not induce the patient to perspire at points of contact. To enhance access to the portion of the patient's tissue near the chest wall that is exposed to the clinician, patient bearing surface 14 may be slightly concave.

Patient bearing surface 14 may also include head support 25, which may be either integrally formed from the padding covering patient bearing surface 14, or may consist of a detachable and removable pillow or cushion fastened to the patient bearing surface by suitable means, such as snaps or Velcro.

Patient bearing surface 14 is fastened to frame 13 around its periphery to tabs 26 (see FIG. 4) which are inwardly disposed from vertical frame elements 22 and top connecting member 23. Patient bearing surface 14 may be fastened to tabs 26 by any suitable means, such as bolts, snaps, or screws, so that patient bearing surface 14 may be readily removed for transit or cleaning of stand 10. In an alternative embodiment, patient support member 14 may comprise a sturdy fiber or breathable plastic mesh material stretched under tension across frame 13, thus further reducing the thickness of the patient bearing surface.

Frame 13 includes hand rail 27 disposed around its circumference, including along horizontal arms 21. Hand rail 26 serves multiple functions in the embodiment of FIGS. 1–4. First, hand rail 26 provides a grip that the patient may use in properly orienting herself with respect to stand 10. Second, the hand rail extending along horizontal arms 21 provides a comfortable surface for the patient to lay her arms atop during the imaging and/or biopsy procedure. Finally, during the more physically and psychologically distressing moments of the biopsy examination, the patient may grip hand rails 26 to obtain a sense of control and security.

In a preferred embodiment of the present invention frame 13 and hand rail 26 are covered with a textured, medium density, self-skinning closed cell foam, e.g., urethane, so that the resulting structure is not unpleasant to the touch. Hand rails 26 may be either permanently affixed to frame 13, or alternatively, may be connected to sections of frame 13 for disassembly when frame 13 is disassembled, as described hereinabove.

Imaging system 30, an illustrative embodiment of which is described hereinafter, is rotatably connected to imaging support column 15. Imaging system 30 provides images of the interior features of the tissue extended through opening 24 using any of a number of technologies, including, for example, radiography, ultrasound and radar. In particular, imaging system 30 may rotated about an axis located parallel to the plane of the compression surfaces of the imaging system, to enable the imaging system to be rotated with respect to the tissue extended through opening 24 of patient bearing surface 14.

Frame 13 is connected to vertical pillar 12 so that the patient becomes inclined in a range of about 5 to 25 degrees, and preferably about 20 degrees, from the vertical when the patient's torso contacts patient bearing surface 14. The patient remains seated while the breast to be examined is extended through opening 24. It is expected that both by gravity and the load created by the patient's body against patient bearing surface 14 will tend to thrust the breast through opening 24, thus enhancing the clinician's access relative to free-hand palpitation.

The significance of allowing the patient to remain seated relates to applicants' findings that certain test subjects report feelings of greater security while oriented in a sitting posture, as opposed to greater feelings of insecurity and vulnerability when lying prone, as is typical for stereotactic biopsy tables. In addition, as described above, inclination of the patient enhances the clinician's access to the patient's tissue in the vicinity of the chest wall.

Referring again to FIG. 1, when patient P is seated on chair 18, she can support the weight of her torso against patient bearing surface 14 while maintaining an inclined seated position. In addition, while patient P may be aware of the presence of the clinician C seated on chair 28 behind stand 10, patient P cannot directly view the activities of the clinician, since her view of the breast extended through opening 24 is shielded by patient bearing surface 14 and frame 13.

Applicant expects that stand 10 will beneficially enable the patient to remain aware of the clinician's presence, thus provide reassurance to the patient, while shielding the patient from a direct view of the tissue being examined. In addition, should patient P experience dizziness or faintness as a result of pain associated with use of biopsy apparatus, known as a vasovagal syncopal response, stand 10 facilitates safe and quick removal of the patient from the stand 10 to a prone position for recovery.

The total floor space occupied by stand 10 and nonslip mat 16 is much less than that required for conventional stereotactic biopsy tables. When used in conjunction with the ultrasound imaging systems described hereinbelow, stand 10 requires none of the shielding required for stereotactic tables, thereby reducing the size and cost of the apparatus relative to previously known devices. In particular, applicants expect that stand 10 in accordance with the present invention may be conveniently used by most smaller health practices with a minimum of dedicated office space.

And because the relatively simple construction of stand 10 enables the apparatus to be produced at lower cost than previously known systems, systems such as described hereinabove may be made more affordable to a larger segment of the health community, in turn increasing the availability of screening to a larger segment of the patient population.

Imaging Apparatus

Figure 5A:
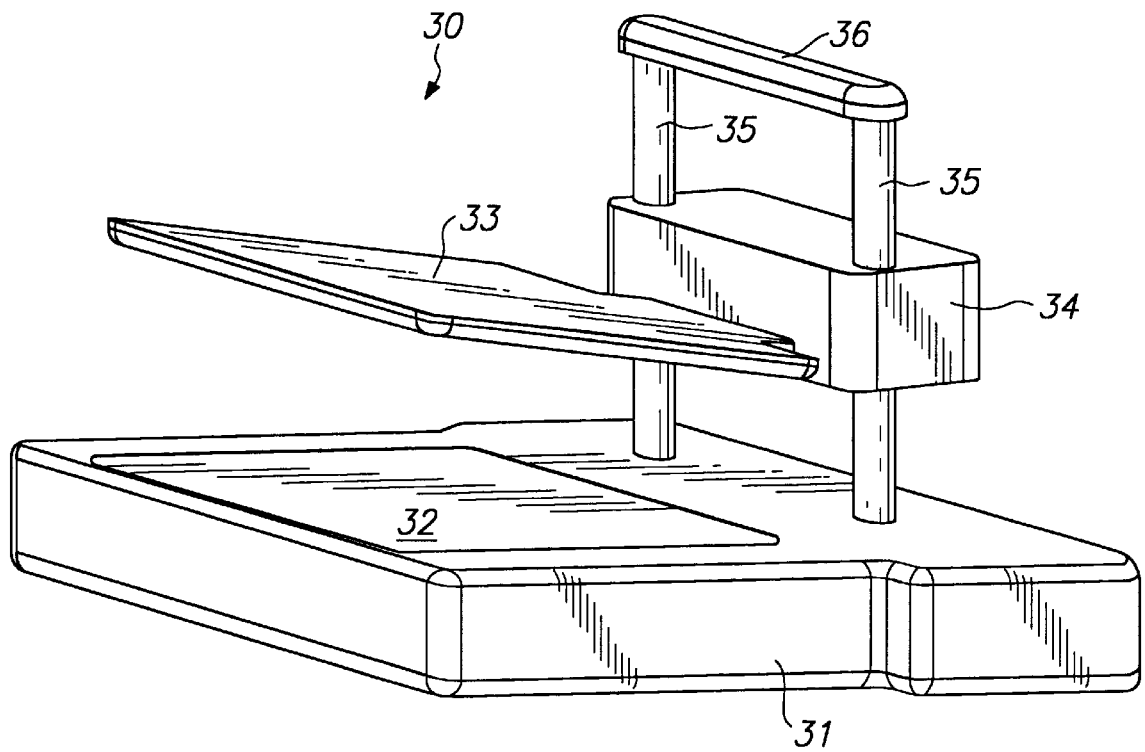
FIGS. 5A and 5B are, respectively, perspective and side views of a the tissue compression and imaging apparatus constructed in accordance with the principles of the present invention.
Figure 5B:
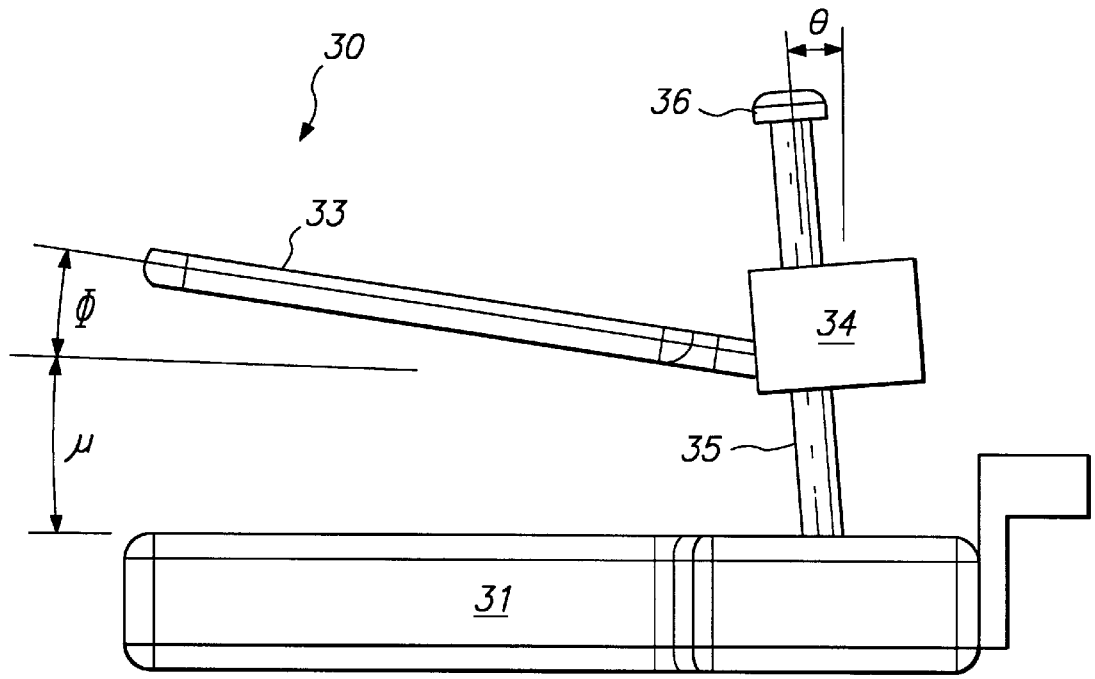

Referring now to FIGS. 5A and 5B, illustrative imaging apparatus 30 constructed in accordance with the present invention is described. In accordance with the principles of the present invention, the compression surfaces of imaging apparatus 30 are arranged so as to induce traction in the patient's tissue that draws the tissue away from the patient's chest during compression. For completeness, the details of the imaging system are first described, after which the features of the imaging system pertinent to the present invention are set forth.

In a preferred embodiment of the present invention, imaging system 30 comprises an ultrasound transducer housed in enclosure 31. The internal arrangement of the ultrasound transducer within enclosure 31 is as described with respect to FIGS. 6, 7 and 13 of commonly assigned U.S. Pat. No. 5,479,927, the entirety of which is incorporated herein by reference.

Imaging system 30 includes sonolucent lower compression plate 32 and upper compression plate 33 affixed to slide block 34. Slide block 34 is adjustably supported on bars 35 so that top block 36 limits the travel of slide block 34 away from enclosure 31. As will of course be understood, the ultrasound transducer is coupled to a microprocessor that displays an image corresponding to the region scanned by the ultrasound transducer.

By way of summary of the disclosure incorporated from U.S. Pat. No. 5,479,927, enclosure 31 contains an ultrasound transducer movably supported on a gantry arrangement so that the ultrasound transducer may be driven to sweep the area of lower compression surface 34, thereby generating a plurality of ultrasonic images orthogonal to the plane of the lower compression surface 32. The ultrasound transducer may comprise a single piston, annular or phased array imaging device of conventional design that preferably operates in a range of about 2 to 15 MHz. More preferably, the ultrasound transducer produces a signal in the transmit mode of a 10 MHz burst having a 100% bandwidth, and may be coupled to the underside of the lower compression plate using a suitable acoustic coupling.

The gantry arrangement contained in enclosure 31 supports a gantry for movement in distal and proximal directions (towards and away from the patient) driven by a motorized track or cable system. The gantry in turn comprises a carriage that supports the ultrasound transducer. The gantry includes motorized drive means for moving the carriage laterally (side-to-side) with respect to the patient's chest wall. As described in the above-incorporated patent, the motorized systems may comprise cable and pulley systems, toothed belts and gear arrangements, threaded blocks carried on a threaded drive rods controlled by encoders and stepper motors, or other suitable means.

Lower compression plate 32 is preferably formed of a sonolucent material, such as Surlyn® ionomers, such as Surlyn® 8940, available from E. I. Du Pont de Nemours and Company, Wilmington, Del., or a polymethyl pentene, such as TPX® MX-002 and MX-004, available from Mitsui & Co., Tokyo, Japan. Upper compression plate may likewise be formed of a sonolucent material, or may be of conventional construction. The above-described ultrasonic imaging system is preferably employed with a gel pad (not shown), that serves to acoustically couple the lower compression surface 32 to the tissue, as described in the above-incorporated U.S. Pat. No. 5,479,927.

Imaging system 30 may alternatively include a conventional radiographic arrangement wherein the X-ray image is converted to a digitized image which is displayed for the clinician's observation.

Referring now to FIG. 5B, a novel feature of the imaging system 30 of the present invention is now described. In FIG. 5B, support bars 35 on which slide block 34 is disposed are canted forward by an angle $\Theta$ of up to about 15 degrees, and preferably about 4 degrees from a plane parallel to the plane of the patient's chest wall. In addition, upper compression plate 33 is inclined at an angle $\Phi$ of up to about 45 degrees, and preferably 4 degrees, from a plane orthogonal to the plane of patient's chest wall. Lower compression surface 32 is angled downward at an angle $\mu$ of up to 90 degrees, and preferably 4 degrees, from that same plane. In one intended use of the ultrasonic scanner of the present invention, wherein the angle $\mu$ is 90 degrees, upper compression plate 33 and bars 35 are removed so that lower compression surface 32 may be pressed directly against the patient's chest wall, for example, for imaging features within the chest wall.

Applicant has determined that by canting support bars 32 towards the patient by an angle $\Theta$, inclining the upper compression plate by an angle $\Phi$, and declining the lower compression plate by and angle $\mu$, a state of traction can be induced in the patient's tissue that draws the tissue away from the patient's chest wall, thereby enhancing the capability to image tissue near the patient's chest wall.

The traction effect induced by the above described system is accomplished as follows: First, the patient inserts the tissue to be examined between the upper compression plate 33 and lower compression surface 32. Next, upper compression plate 33 is lowered by moving slide block 34 down support bars 35 until upper compression plate 33 contacts the tissue. As slide block 34 and upper compression plate 33 are urged further towards lower compression surface 32, the tissue becomes flattened.

Due to the cant of support bars 35, continued downward movement of upper compression plate 33 causes the upper compression plate to be displaced away from the patient's chest wall, thereby inducing a traction force in the tissue contacting the upper compression plate. This traction force tends to pull the tissue away from the chest wall, permitting enhanced imaging capability.

Applicant's invention represents a subtle but significant departure from previously known compression arrangements, wherein the compression plates typically move orthogonally during the tissue compression step. In such previously known systems, when a compressive load imposed on the tissue, the tissue is generally forced outwardly, thus causing the tissue near the chest wall to be forced inwardly, i.e., into the patient's chest cavity. As described hereinabove, the method of canting and inclining the components of the imaging system provides improved imaging capability with respect to previously known systems.

While the present invention has been described hereinabove in the context of an ultrasonic imaging system, it will be apparent to those of skill in the art that this feature of the present invention may provide significant imaging enhancement when used in conventional mammography systems.

Image-Guided Biopsy Apparatus

Referring now to FIGS. 6 through 8, illustrative biopsy apparatus constructed in accordance with the principles of the present invention is described. This biopsy apparatus provides the capability to perform biopsy under the guidance of real-time ultrasonic images of the tissue.

A preferred embodiment of the biopsy system for use with stand 10 and imaging system 30 of the present invention is described in co-pending and commonly assigned U.S. patent application Ser. No. 08/421,381, which is incorporated herein by reference in its entirety. In the biopsy system described in that application, a biopsy device is guided to a target location within the patient's tissue using ultrasonic images displayed on a display screen monitored by the clinician. The imaging system therein described employs an ultrasonic scanner having the components described hereinabove with respect to FIG. 5.

The biopsy device, which may be a biopsy needle, biopsy gun or similar device having a cannula to obtain a tissue core, is fastened to an electronic tracking arrangement that produces an indicator of the location of the tissue-effecting end of the biopsy device, i.e, needle or center of cannula, which is superimposed on a display of the ultrasound image of the tissue. In accordance with the system described in the above-incorporated application, the needle or cannula trajectory may be determined prior to actual insertion of the device into the tissue, thereby reducing the need for repeatedly inserting and withdrawing the device to obtain samples of a suspected lesion.

Referring now to FIGS. 6 through 8, alternative embodiments of a biopsy and imaging system are described to that disclosed in the above-incorporated application Ser. No. 08/421,381, and which provide ultrasonic scanning and image-guided biopsy using conventional ultrasound transducers.

Figure 6A:
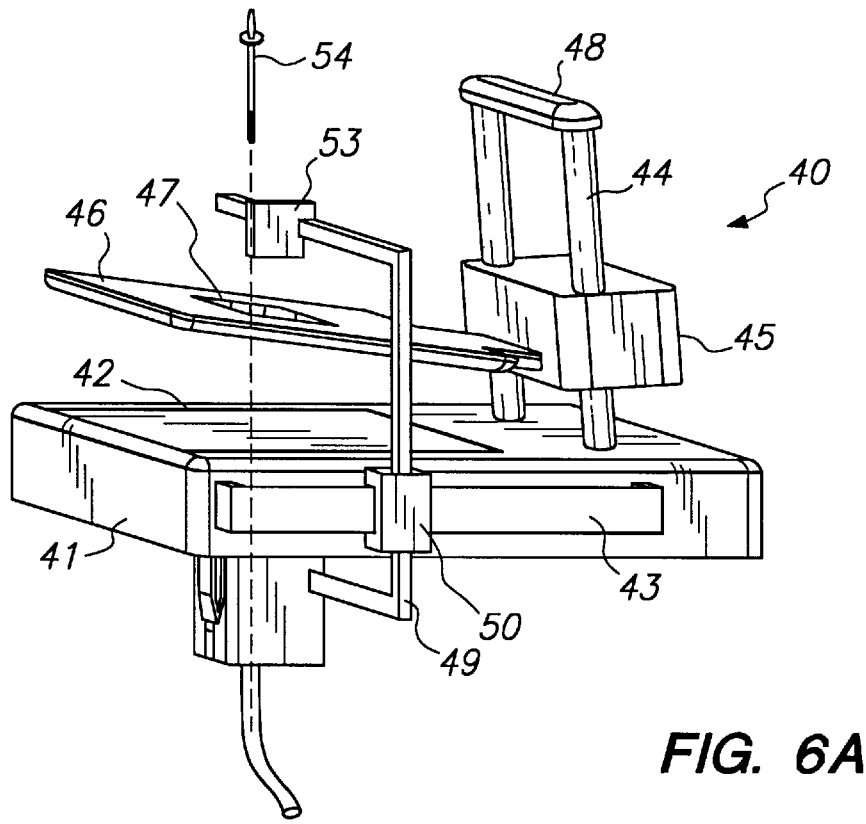
FIGS. 6A and 6B are, respectively, perspective and front sectional views of a first illustrative imaging and biopsy apparatus constructed in accordance with the present invention.
Figure 6B:
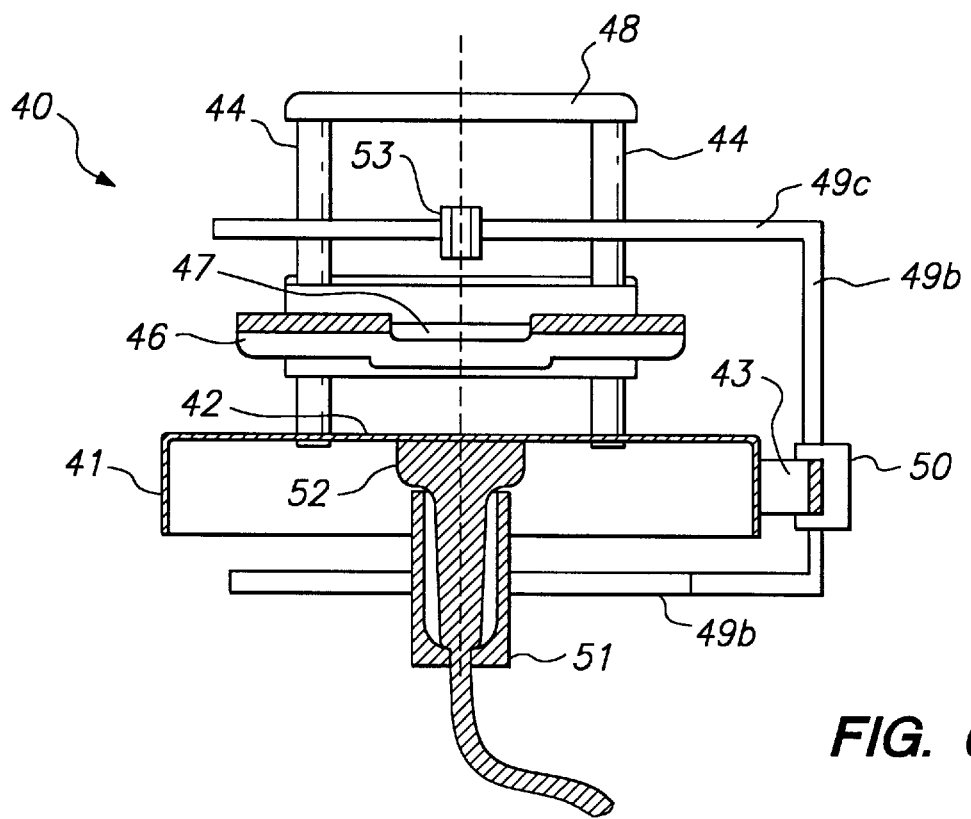

With respect to FIGS. 6A and 6B, a first embodiment of an image-guided biopsy system constructed in accordance with the present invention is described.

Biopsy system 40 includes rigid housing 41 including sonolucent lower compression plate 42 and guide arm 43. Support bars 44 are affixed to housing 41 and vertically adjustably support slide block 45 and upper compression plate 46. Upper compression plate 46 includes window 47 through which the needle or cannula of a biopsy device may be inserted, as described hereinafter. Top block 48 limits upward travel of slide block 45 on support bars 44. Support bars 44 are canted forward by an angle $\Theta$, upper compression plate is inclined at an angle $\Phi$, and lower compression plate 42 is declined at an angle $\mu$, as described hereinabove with respect to FIG. 5.

Guide arm 43 includes a C-shaped support arm 49 which is fastened to slide block 50. Slide block 50 is disposed for proximal and distal movement along guide arm 43. C-shaped support arm 49 includes lower arm 49a, vertical arm 49b and upper arm 49c. Lower arm 49a carries holder 51 which is configured to hold an ultrasound transducer 52 so that it is acoustically coupled to the underside of lower compression plate 42. Upper arm 49c includes biopsy device support block 53 for removably carrying a biopsy device, such as needle 54, as described in the above-incorporated U.S. application Ser. No. 08/421,381.

Still referring to FIG. 6, biopsy device support block 53 on C-shaped support arm 49 holds biopsy device 54 so that the needle or center of the cannula of the device is aligned with ultrasound transducer 52. Ultrasound transducer, which may be of conventional design, is connected to a suitable processor and display (not shown) for generating an ultrasound image that is orthogonal to the plane of lower compression plate 42. When the biopsy device is pressed against the upper surface of the tissue, or inserted into the tissue, the needle or cannula will be visible in the ultrasound image displayed for the clinician's viewing. Accordingly, biopsy device 54 may be guided to a selected region of the tissue under guidance of the ultrasound image generated by ultrasound transducer 52.

C-shaped support arm 49 provides additional advantages for use in imaging and biopsying tissue, as will now be described. Holder 51, ultrasound transducer 52 and biopsy device support block 53 are maintained in relative alignment along a plane substantially parallel to the patient's chest by C-shaped support arm 49. Thus, when slide block 50 is moved along guide arm 43, the clinician is able to obtain and display images of the tissue to conduct a thorough examination.

In addition holder 51 and biopsy device support block 53 may be moved laterally along lower arm 49a and upper arm 49c, respectively, while still maintaining proximal and distal alignment of the biopsy device with the ultrasound image, i.e., both elements remain in the same plane relative to the chest wall. Further, the trajectory of the biopsy device may be determined in the ultrasound image simply by contacting the needle or cannula to the tissue, thus allowing biopsy device support block 53 to be moved along upper arm 49c to position the biopsy device.

The embodiment of FIGS. 6A and 6B provides much of the functionality described with respect to the previously described embodiment, but with lower cost components. In particular, because biopsy system 40 employs a conventional ultrasound transducer that is manually moved to scan the tissue, much of the drive circuitry and electronic tracking apparatus of the previously described embodiment may be omitted.

Figure 7A:
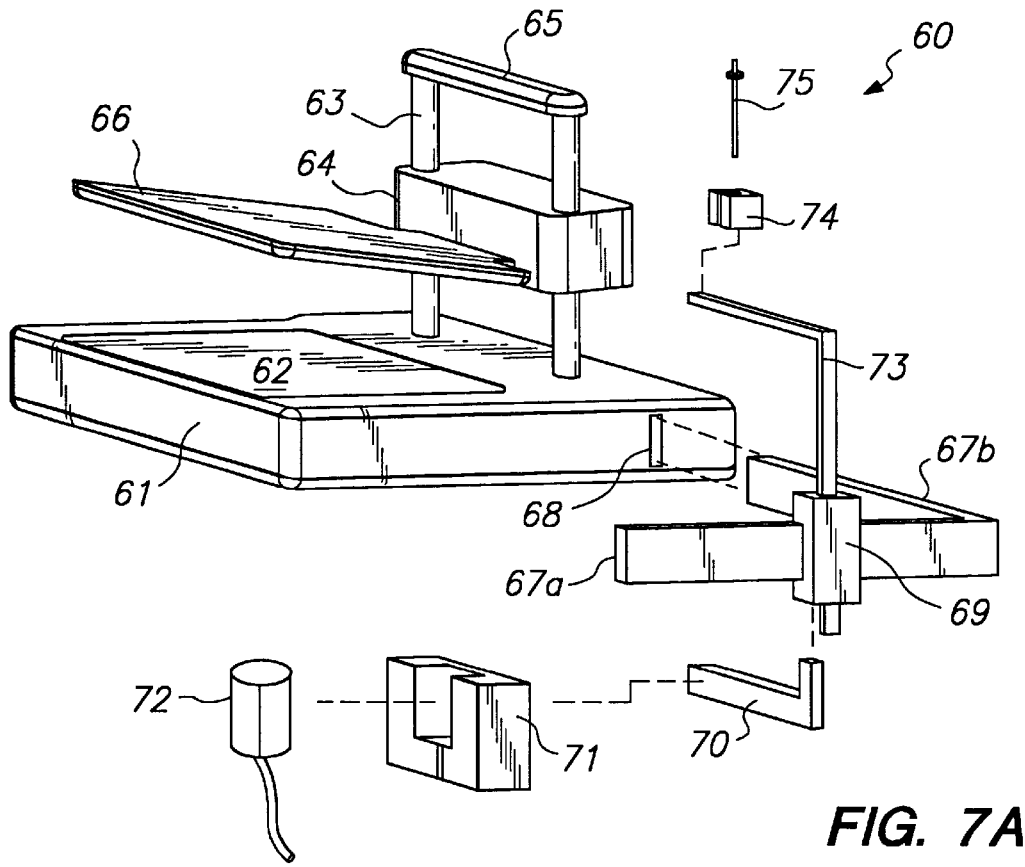
FIGS. 7A and 7B are, respectively, perspective and front sectional views of a second illustrative imaging and biopsy apparatus constructed in accordance with the present invention.
Figure 7B:
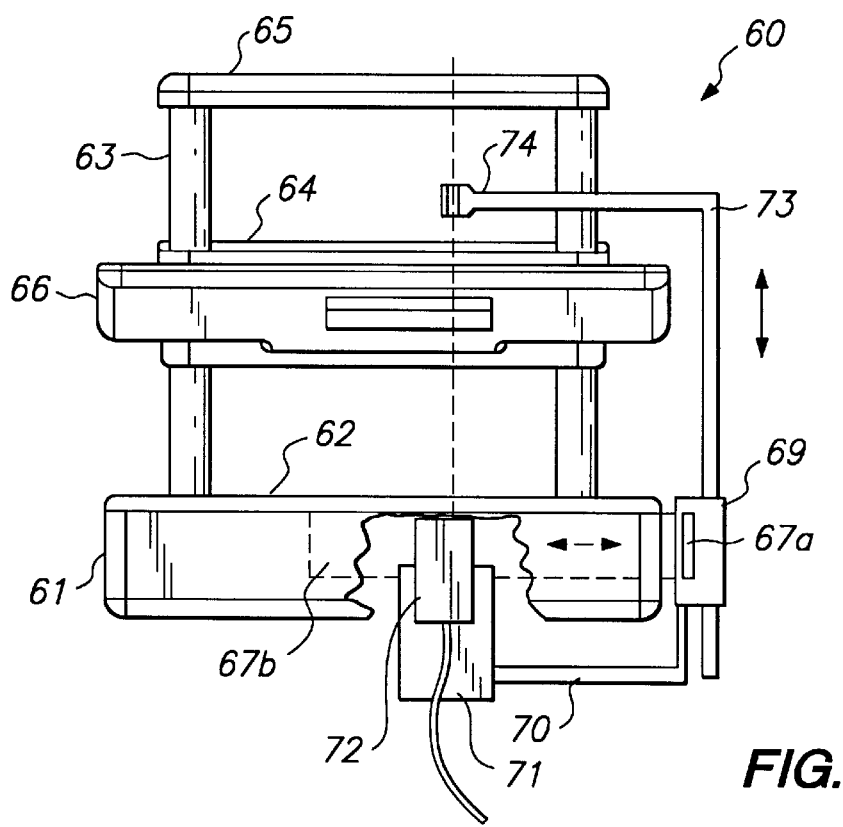

Referring now to FIGS. 7A and 7B, an alternative embodiment of a biopsy system is described, in which complete alignment of the ultrasound transducer and biopsy device support is maintained. Biopsy system 60 of FIGS. 7A and 7B includes rigid housing 61 including sonolucent lower compression plate 62, support bars 63, slide block 64, top block 65, and upper compression plate 66 arranged as described for biopsy system 40 of FIG. 6. Support bars 63, upper compression plate 66 and lower compression plate 62 are configured as described hereinabove with respect to FIG. 5.

Guide arm 67 comprises an L-shaped member having first leg 67a disposed parallel to the lateral surface of housing 61 and second leg 67b slidably disposed in slot 68 in housing 61. Connector block 69 is slidably disposed on first leg 67a of guide arm 67 for movement towards and away from the patient's chest.

Connector block 67 carries transducer support arm 70 which in turn supports holder 71 in which ultrasound transducer 72 is disposed. Connector block 69 also provides a bore through which L-shaped support rod 73 is adjustable carried. Biopsy device support block 74 is disposed on an end of L-shaped support rod 73 for carrying a biopsy device, such as needle 75. As shown in FIG. 7B, biopsy device support block 74 holds the biopsy device so that the needle or cannula of the biopsy device is aligned with the image field of ultrasound transducer 72.

Second leg 67b is supported within housing 61 by suitable elements so that second leg 67b may be moved in a plane parallel to the patient's chest to adjust the side to side positioning of ultrasound transducer 72 and biopsy device support block 71 while maintaining these components in alignment. In addition, L-shaped support rod 73 may be vertically adjusted relative to the upper compression plate to vary the height of the biopsy device support block above the patient's tissue.

Unlike the embodiment of FIG. 6, the embodiment of FIG. 7 maintains complete alignment of biopsy device support block 74 and ultrasound transducer 72, even during side-to-side movement of the scanner, by translating the entire arrangement in connection with movement of second leg 67b of guide arm 67. The embodiment of FIG. 7 therefore not only provides the image-guided functionality of previously described embodiments, but retains complete alignment of the biopsy device and the ultrasound image.

Figure 8A:
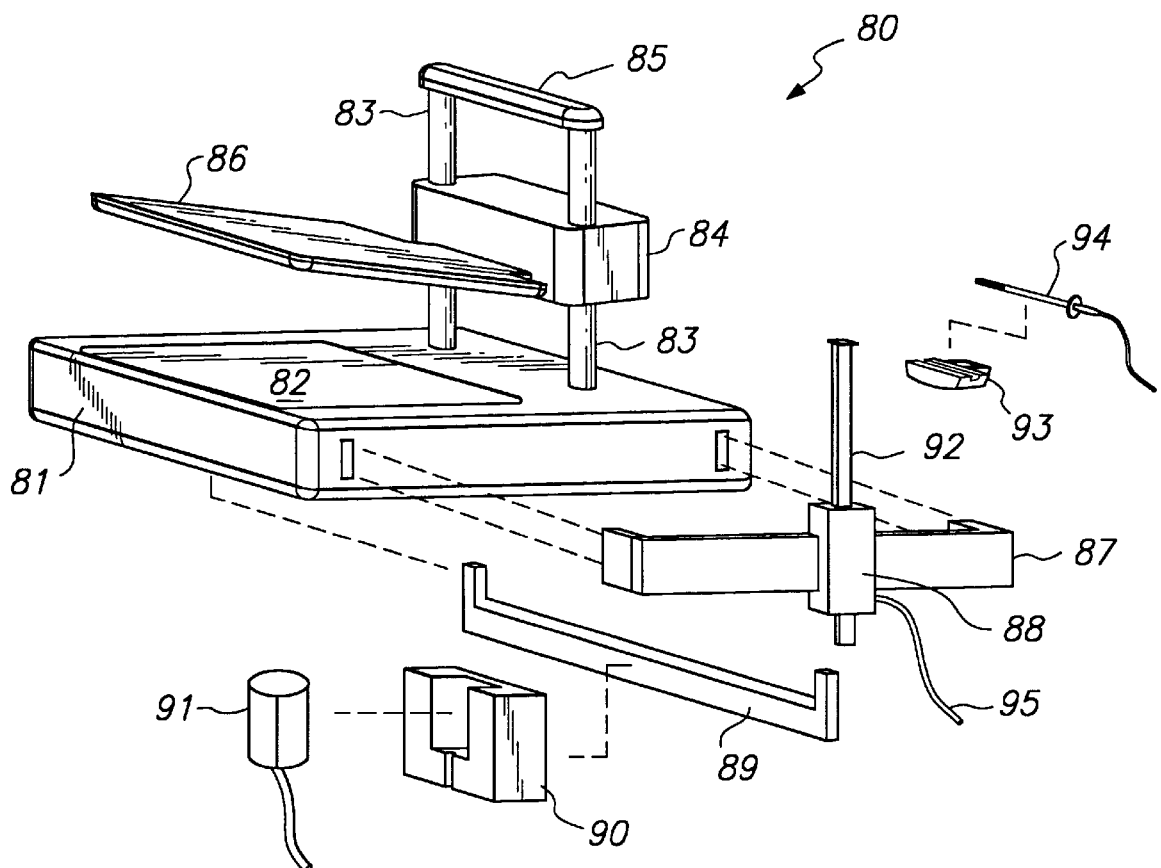
FIGS. 8A and 8B are, respectively, perspective and front sectional views of a third illustrative imaging and biopsy apparatus constructed in accordance with the present invention.
Figure 8B:
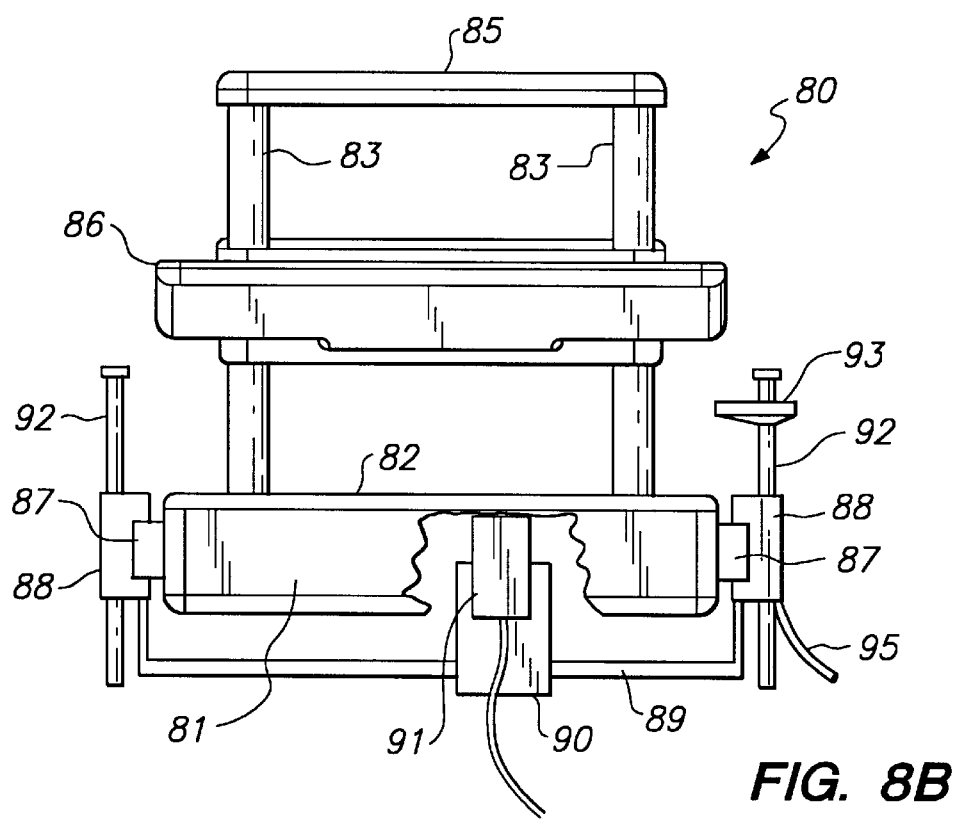

Referring now to FIGS. 8A and 8B, yet another alternative embodiment of a biopsy system is described, in which alignment of the ultrasound transducer and biopsy device support is maintained partly by mechanical alignment and partly by electronic tracking. Biopsy system 80 of FIGS. 8A and 8B includes rigid housing 81 including sonolucent lower compression plate 82, support bars 83, slide block 84, top block 85, and upper compression plate 86 arranged as described for biopsy system 40 of FIG. 6. Support bars 83, upper compression plate 86 and lower compression plate 82 are configured as described hereinabove with respect to FIG. 5.

Guide arm 87 is affixed to one or both sides of housing 81 (only one such guide is shown for clarity in FIG. 8A). Connector block 88 carries transducer support arm 89 which in turn supports holder 90 in which ultrasound transducer 91 is disposed. Connector block 88 also provides a bore through which support rod 92 is adjustably carried. Biopsy device support block 93 is disposed on an end of support rod 92 for carrying a biopsy device, such as needle 94.

As will be apparent from FIG. 7B, transducer support arm 89 aligns ultrasound transducer 91 with biopsy device support block 93 in a plane parallel to the patient's chest wall. In a preferred embodiment, support rod 92 has disposed within it a printed circuit board arrangement of parallel, spaced-apart copper strips and connector block 88 includes a linear encoder that senses the static capacitance of the copper strips as the encoder is manually slid through connector block 88.

Thus, as support rod 92 is moved through connector block 88, the linear encoder outputs a signal corresponding to its displacement from a preset reference point, preferably, the upper surface of lower compression plate 82. The signal output by linear encoder is provided to a computer (not shown) via connecting cable 95. The linear encoder preferably has a displacement accuracy of about plus/minus 0.05 mm, and is available from Sylvac S. A., Crissier, Switzerland, and distributed in the United States by Fowler Company, Inc., Chicago, Ill., as Part No. 54-050-000.

Biopsy system 80 of FIG. 7 provides partial alignment of the biopsy device support block 93 with ultrasound transducer 91 through the connection of transducer support arm 89 to connector block 88. Thus, the clinician is assured that the needle or cannula trajectory of the biopsy device will intercept the tissue displayed in the ultrasound image. In addition, the use of a linear encoder in conjunction with connector block 88 enables the vertical height of biopsy device to be determined and the needle or cannula trajectory to be displayed superimposed on the ultrasound image of the tissue as described in the above-incorporated U.S. application Ser. No. 08/421,381.

It will be understood that the foregoing is merely illustrative of the apparatus and methods of the present invention, and that various modifications can be made by those skilled in the art without departing from the scope and spirit of the invention.

What is claimed is:

1. A stand for conducting an examination of breast tissue, the stand comprising:

a base;

a pillar connected to the base;

footrests connected to the pillar that support a patient's legs when a patient is seated adjacent to the stand;

a frame connected to the pillar, the frame defining an opening and comprising:

first and second substantially horizontal arms having proximal and distal ends, the distal end of each one of the first and second substantially horizontal arms connected to the pillar so that the proximal ends of the first and second substantially horizontal arms project away from the pillar in spaced-apart parallel relation;

first and second vertical frame members having upper and lower ends, the lower end of the first vertical frame member connected to the proximal end of the first substantially horizontal arm, the lower end of the second vertical frame member connected to the proximal end of the second substantially horizontal arm, the upper ends of the first and second vertical frame members projecting upwardly away from the first and second substantially horizontal arms, respectively, in spaced-apart parallel relation; and a top connecting member having first and second ends, the first end connected to the upper end of the first vertical frame member and the second end connected to the upper end of the second vertical frame member;

a patient bearing surface disposed within the opening and attached to the frame, the patient bearing surface being inclined from a vertically-oriented plane, the patient bearing surface defining an aperture through which a breast of a patient may be extended, the patient bearing surface partially supporting the weight of a patient's upper torso when the patient is seated adjacent to the stand and inclined upon the patient bearing surface.

2. The stand as defined in claim 1 wherein the patient bearing surface comprises a layer of closed cell medium density foam.

3. The stand as defined in claim 1 further comprising a hand rail disposed along the periphery of the frame.

4. The stand as defined in claim 1 further comprising an imaging system support column affixed to the pillar, and an ultrasonic imaging system mounted on the imaging system support column for rotation about an axis aligned with the aperture in the patient bearing surface.

5. The stand as defined in claim 1 wherein the frame may be disassembled for transportation.

6. The stand as defined in claim 4 wherein the imaging system comprises a first compression surface, a second compression surface, and means for moving the first compression surface toward the second compression surface, the means for moving arranged so that the first compression surface is displaced relative to the second compression surface away from a patient's chest wall as the first compression surface moves toward the second compression surface.

7. The stand as defined in claim 6 wherein the first compression surface is inclined at an angle inward towards the patient's breast, relative to a plane orthogonal to the patient's chest wall.

8. The stand as defined in claim 6 wherein the second compression surface is inclined at an angle inward towards the patient's breast, relative to a plane orthogonal to the patient's chest wall.

9. The stand as defined in claim 4 further comprising a biopsy system connected to the imaging system support column, the biopsy system enabling a clinician to conduct a biopsy guided by ultrasound images.

10. The stand as defined in claim 9 wherein the biopsy system comprises an ultrasound transducer, a biopsy device support block, and a connecting member that maintains alignment of the ultrasound transducer and the biopsy device support block in at least one plane.

11. The stand as defined in claim 10 wherein the connecting member comprises a C-shaped support arm having first and second legs, the ultrasound transducer carried on a first leg and the biopsy device support block carried on the second leg.

12. The stand as defined in claim 9 wherein the connecting member maintains alignment of the ultrasound transducer and the biopsy device support block in at least two orthogonal planes.

13. The stand as defined in claim 12 wherein the connecting member comprises a transducer support arm, a connector block and an L-shaped support rod, the ultrasound transducer carried on a transducer support arm and the biopsy device support block carried on the L-shaped support leg.

14. The stand as defined in claim 10 wherein the biopsy system further comprises encoder means for determining the vertical height of the biopsy device support block relative to the lower compression plate.

* * * * *